(12) United States Patent
Sweeney

(10) Patent No.: US 9,282,975 B2
(45) Date of Patent: Mar. 15, 2016

(54) DRILL BIT AND METHOD FOR PREPARING A BONE FOR A FIXATION SCREW

(71) Applicant: Spinal Generations, LLC, Mokena, IL (US)

(72) Inventor: Patrick J. Sweeney, Flossmoor, IL (US)

(73) Assignee: Spinal Generations, LLC, Mokena, IL (US)

(*) Notice: Subject to any disclaimer, the term of this patent is extended or adjusted under 35 U.S.C. 154(b) by 152 days.

(21) Appl. No.: 14/137,092

(22) Filed: Dec. 20, 2013

(65) Prior Publication Data

US 2015/0173775 A1    Jun. 25, 2015

(51) Int. Cl.
*A61B 17/00* (2006.01)
*A61B 17/16* (2006.01)

(52) U.S. Cl.
CPC .................. *A61B 17/1615* (2013.01)

(58) Field of Classification Search
None
See application file for complete search history.

(56) References Cited

U.S. PATENT DOCUMENTS

2013/0116693 A1* 5/2013 Nelson et al. ...... A61B 17/7233
606/64

* cited by examiner

*Primary Examiner* — Sameh Boles
(74) *Attorney, Agent, or Firm* — Foley & Lardner LLP

(57) ABSTRACT

A method of preparing a bone to receive a fixation screw through a fixation device includes providing a drill bit sized and configured to pass through a bore in a fixation device positioned in the bone and drilling a passage into the bone and through the bore. At least a distal portion of the drill bit passes through the bore in the drilling step. At least an outer portion of the distal portion of the drill bit has a hardness that is less than a hardness of the fixation nail.

9 Claims, 5 Drawing Sheets

DRILL BIT AND METHOD FOR PREPARING A BONE FOR A FIXATION SCREW

BACKGROUND

Devices such as intramedullary rods, bone nails, bone screws, plates, etc. may be affixed to a bone to repair or strengthen fractured or otherwise damaged or diseased bones, often by fixing two or more bones or bone pieces with respect to each other, in which case the device may be referred to as a fixation device. Such fixation devices share the load with the bone to support the bone as it heals. The fixation device may be further adapted to deliver medication or other fluids into bone.

For unthreaded, smooth-sided devices, secondary fixation devices such as screws may be used to rotationally fix the fixation device to the bone. These screws are generally oriented orthogonally with respect to the fixation device and pass through bores formed in the fixation device. A drill is used to form a passage in the bone, the passage extending through the bore in the fixation device. The drill bits used for such procedures are typically formed of a similar material to the fixation device itself, such as a stainless steel or titanium alloy or a material that is harder than the material from which the fixation device is formed.

If the drill is improperly oriented during the drilling procedure or if the drill bit is too large in diameter relative to the bore, the drill bit may contact a portion of the fixation device (e.g., the portion of the fixation device surrounding the bore) and cause scoring or other physical damage to the fixation device. Such physical damage can compromise the effectiveness of the fixation device, such as by physically weakening the fixation device in a high stress area or by affecting the delivery of medication or other fluids to the bone.

SUMMARY

One embodiment of the invention relates to a method of preparing a bone to receive a fixation screw through a fixation device. The method includes providing a drill bit sized and configured to pass through a bore in a fixation device positioned in the bone and drilling a passage into the bone and through the bore. At least a distal portion of the drill bit passes through the bore in the drilling step. At least an outer portion of the distal portion of the drill bit has a hardness that is less than a hardness of the fixation nail.

Another embodiment of the invention relates to a bone fixation system including a fixation device configured to be positioned at a target area of bone and a drill bit. The fixation device includes two ends connected by a shaft and includes a bore formed through the shaft configured to receive a fixation screw. The drill bit is sized and configured to pass through the bore to prepare the surrounding bone to receive a second fixation device. At least a distal portion of the drill bit is configured to pass through the bore. The fixation device is made of a first material and the distal portion of the drill bit comprises at least an outer portion made of a second material. The second material of the drill bit has a hardness that is less than the hardness of the first material of the fixation device.

Another embodiment of the invention relates to a drill bit for preparing a hole in a bone. The drill bit includes a drill bit shaft having a distal portion sized and configured to be received through a bore in a fixation device. The distal portion has a hardness of between the hardness of the bone and the hardness of the stainless steel, or less than the hardness of the stainless steel.

Alternative exemplary embodiments relate to other features and combinations of features as may be generally recited in the claims.

BRIEF DESCRIPTION OF THE DRAWINGS

The disclosure will become more fully understood from the following detailed description, taken in conjunction with the accompanying figures, wherein like reference numerals refer to like elements.

DETAILED DESCRIPTION

Referring generally to the figures, a cannulated fixation nail (e.g., bone nail, intramedullary nail, intramedullary rod, intramedullary pin, etc.) is configured to stabilize a bone or multiple bones by holding two or more bones or bone pieces in a fixed spatial relationship with respect to each other. The bone nail may be coupled to the exterior surface of the bone or may be disposed in an interior portion (e.g., the medullary canal) of the bone. The bone nail may be secured with one or more fixation devices, such as bone screws that engage both the bone nail and the surrounding bone tissue. The bone nail and/or the bone screw may be cannulated and used to deliver desired substances to the vicinity of a bone. In certain embodiments, the nail and/or the screws may also be fenestrated or permeable to the substance to be delivered. The substances to be delivered may include medicants or therapeutics, or other substances which are desirable to deliver to the vicinity of a bone. The substance or a combination of substances may be delivered to the interior of a bone, to the exterior of a bone, to the fracture interface between two or more broken bones, or to any other location.

A nail or screw may be "cannulated" in that it includes a hollow cavity disposed inside at least part of its shaft. For example, the cavity may consist of a bore beginning at or near one end of the nail or screw and extending longitudinally into the nail or screw. Other configurations are possible, however, and the hollow cavity need not be restricted to a cylindrical shape or a circular cross-section. The cavity may extend throughout the entire length of the nail or screw, thus creating openings at each end of the nail or screw, or alternatively, the cavity may extend only partially into the interior of the nail or screw. The shape and size of the cavity may be suitably chosen to allow delivery of the desired substance through the nail or screw to the bone area of interest. When it is desired to use the cannulated portion of the nail or screw as reservoir for the substance to be delivered, for example, the cavity may be made as large as possible so long as the screw and insert maintain the structural integrity needed for introduction into the bone.

As used herein, the term "bone screw" is intended to refer to screws of all types which are presently known or hereafter devised for implantation into bone. In this regard, cancellous screws, cortical screws, and machine screws are all contemplated as being within the scope of bone screws. Bone screws typically include threads along at least a portion of the exterior of the screw shaft, but it should be appreciated that tacks, pins, nails and the like may also be included within the definition of a bone screw, whether threaded or unthreaded. When threads are present, it may be found advantageous to use self-tapping threads, or alternatively, the threads can be pre-cut in the bone prior to bone screw insertion.

Figure 1:
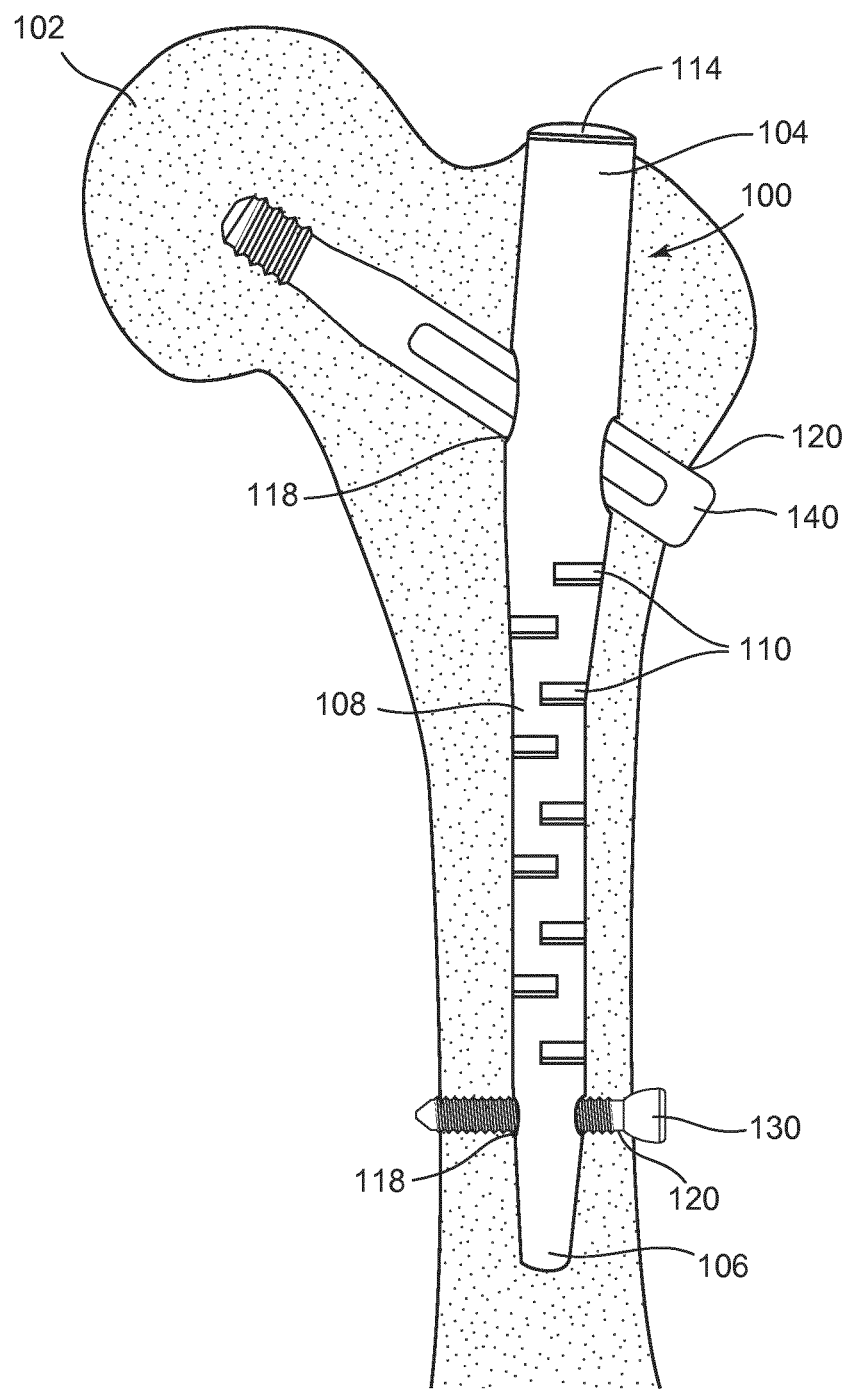
FIG. 1 shows a fixation system including a fixation nail inserted into the femur bone of a patient and secured by fixation screws, according to an exemplary embodiment.
Figure 2:
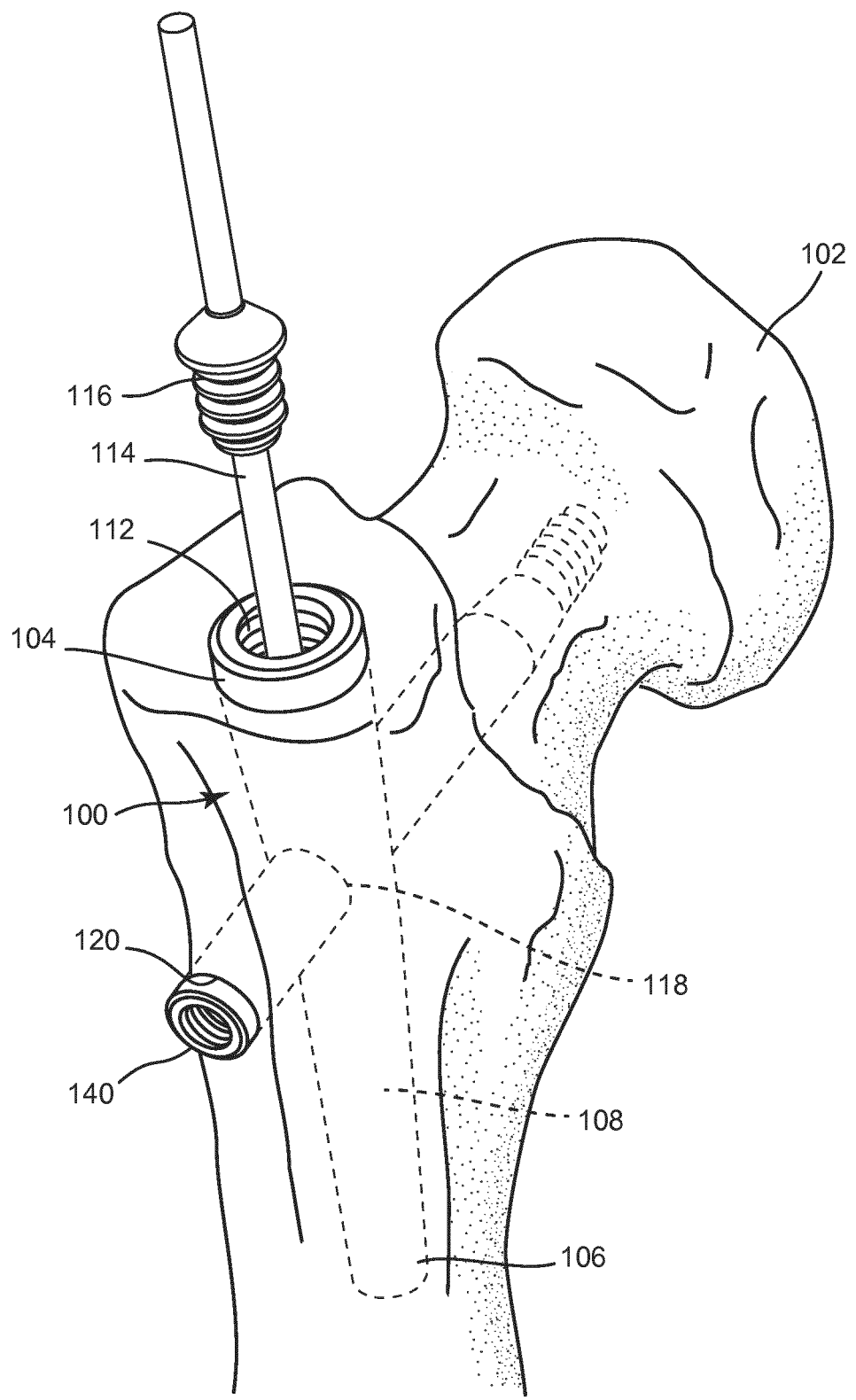
FIG. 2 shows a perspective view of a bone screw insert being inserted into the fixation nail of FIG. 1.
Figure 3:
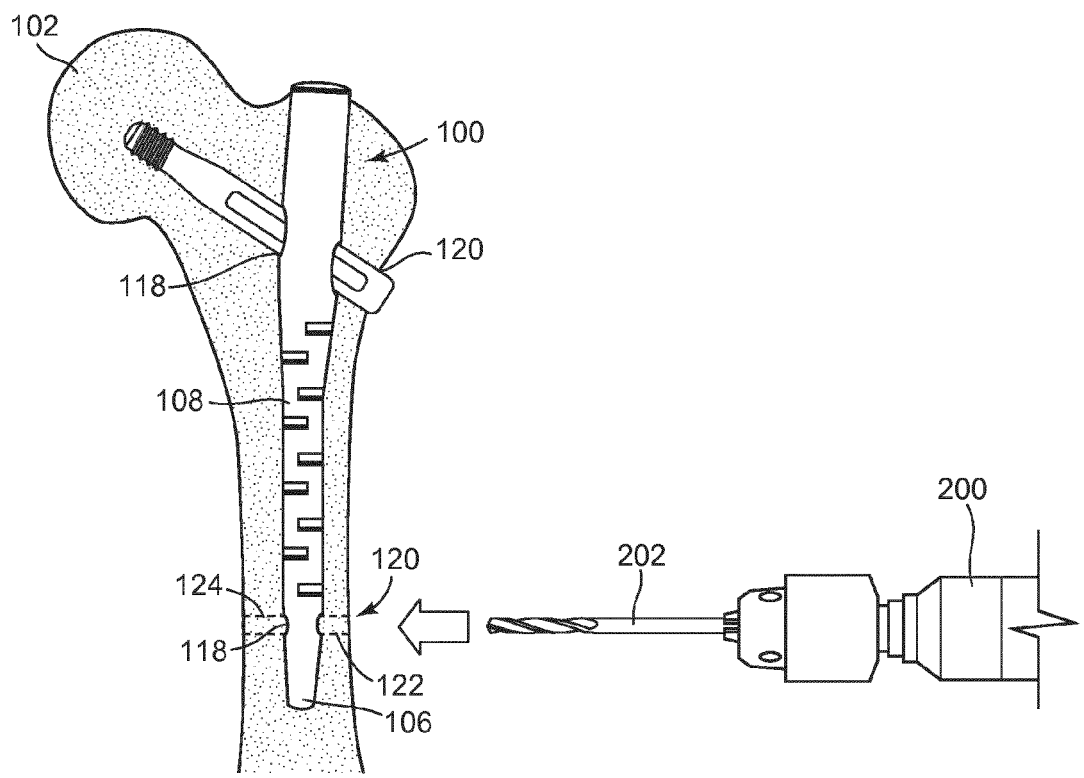
FIG. 3 shows a drill forming a passage for a fixation screw of the fixation system of FIG. 1.

Referring to FIGS. 1-3, a fixation system includes a fixation device, shown as a fixation nail 100 disposed within a bone 102. As shown in FIG. 1 according to one embodiment, the fixation nail 100 is disposed in the intramedullary cavity of the femur. In other embodiments, the fixation system may be utilized to stabilize any other suitable bone, such as a humerus, tibia, etc. The fixation nail 100 may be disposed in the interior of the bone 102 or may be disposed along the exterior surface of the bone 102.

The fixation nail 100 has two ends 104 and 106 connected by a shaft 108. All or a portion of the shaft 108 may be cannulated. The shaft 108 of the fixation nail 100 may include fixation nail fenestrations 110, through which a substance may pass from the cannulated shaft 108 to the surrounding bone tissue. The substance provided to the bone may be, for example, medicants or therapeutics, or other substances which are desirable to deliver to the vicinity of a bone. One end of the fixation nail 100 may be configured to accept a nail insert 114. This is demonstrated in FIG. 2 which shows a perspective view of the fixation nail 100 having internal threads 112 on one end 104 to promote fixation of the nail insert 114 having threads 116 on one end.

The fixation nail 100 may be formed of any material suitable for placement into a bone without harmful effects on the patient. Examples of suitable materials include, but are not limited to titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalcium-phosphate. Other materials useful for bone nail construction will be known to those skilled in the art, and are to be included within the scope of the present invention.

The bores 118 may be defined in the walls of the shaft 108 along the length of the fixation nail 100. The bores 118 provide apertures through which second fixation devices, shown as fixation screws 130 and 140, may be passed in order to affix the fixation nail 100 to the bone 102. According to an exemplary embodiment, the bores 118 are oriented such that the fixation screws 130 or 140 pass through the fixation nail 100 substantially perpendicular to the longitudinal axis of the fixation nail 100. In another embodiment, the bores 118 are oriented such that the fixation screws 130 or 140 pass through the fixation nail 100 at acute or obtuse angles with respect to the longitudinal axis of the fixation nail 100. The dimensions of a fixation screw that passes through the cannulated portion of a fixation nail are desirably selected such that the screw does not substantially impede the passage of a substance to be delivered to the bone.

In one embodiment, the screws 130 and 140 include an elongated shaft that is sized to pass through the bore 118. In some instances, the fixation screws 130 and 140 may be cannulated and include a longitudinal bore that allows for the passage of the substance. In one embodiment, the screws 130 and 140 include external threads along at least a portion of the exterior of the shaft that pass through the bore 118 and are configured to engage the bone tissue. The screws 130 and 140 may be any suitable threaded fastener known in the art, including cancellous screws, cortical screws, and machine screws. In other embodiments, the fixation nail 100 may be affixed to the bone 102 with a non-threaded fixation device, such as tacks, pins, nails and the like.

The screws 130 and 140 may be formed of any material suitable for placement into a bone without harmful effects on the patient. Examples of suitable materials include, but are not limited to titanium and its alloys, tantalum and its alloys, nickel-cadmium and its alloys, steel and its alloys, plastics, absorbable materials, resorbable materials, polyamino acids, polylactide, polyglycolide, hydroxylapatite, and tricalcium-phosphate. Other materials useful for bone screw construction are known to those skilled in the art, and are to be included within the scope of this disclosure.

Referring now to FIG. 3, passages 120, aligned with each of the bores 118, are formed in the bone 102 with a drill 200 having a drill bit 202. The passages 120 are configured to receive the screws 130 and 140. The drill 200 may be a positioned relative to the fixation nail 100 with an external structure (e.g., bracket, arm, fixture, etc.) to maintain the alignment between the passage 120 and the respective bore 118. The drill 200 is activated to rotate the drill bit 202, which is advanced into the bone 102. As the drill bit 202 is advanced into the bone 102, it removes bone tissue to form the passage 120. The drill bit 202 passes through the bore 118 and forms a passage 120 with a first portion 122 on one side of the fixation nail 100 and a second portion 124 on the opposite side of the fixation nail 100. Once the passage 120 is formed, the drill bit 202 is withdrawn from the bone 102. The screw 130 or 140 may then be advanced through the passage 120 and the bore 118 to engage the bone 102 and secure the fixation nail 100 to the bone 102.

Figure 4:
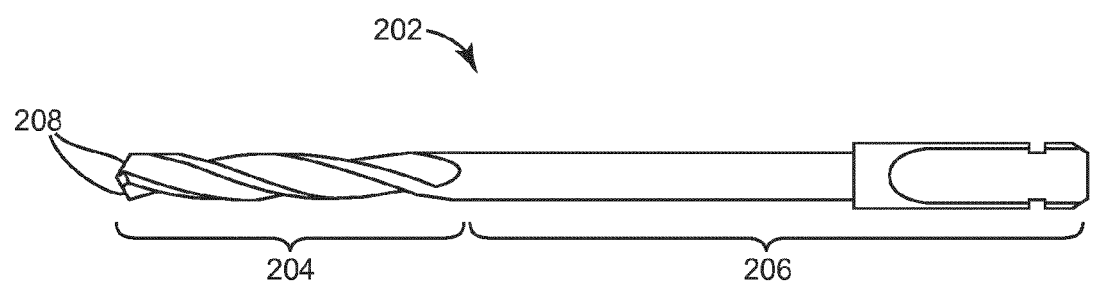
FIG. 4 shows a side view of a drill bit for forming a passage for a fixation screw of the fixation system of FIG. 1, according to an exemplary embodiment.

Referring now to FIG. 4, the drill bit 202 is shown according to an exemplary embodiment. The drill bit 202 includes a drill body 204 (distal portion) with cutting edges 208 that are configured to cut and remove material from the passage 120 and a shank portion 206 (proximal portion) that is engaged by a drive mechanism of the drill 200. The drill bit 202 is formed from a material suitable for placement into a bone without harmful effects on the patient. According to an exemplary embodiment, at least a portion of the drill bit 202 including the cutting edges 208 is formed of a material with a hardness that is less than the hardness of the material used to form the fixation nail 100. Because the hardness of the portion of the drill bit 202 including the cutting edges 208 is less than the hardness of the fixation nail 100, the drill bit 202 will not damage the fixation nail 100 if it inadvertently contacts the fixation nail 100 while forming the passage 120 (e.g., contacting the portions of the shaft 108 surrounding the bores 118). The drill bit 202 may be configured to be reusable and sterilized after each use or the drill bit 202 may be configured to be disposable and be replaced after use.

The material(s) chosen to form the drill bit 202 may vary depending on the material of the components of the fixation system, such as the fixation nail 100. According to an exemplary embodiment, the fixation nail 100 is formed from a austenitic stainless steel (e.g., 316LVM stainless steel), which has a hardness of approximately 160 HB. At least a portion of the drill bit 202 for use with such a fixation nail may therefore be formed of a material with a hardness that is less than approximately 160 HB, such that it does not damage the fixation nail, but greater than the hardness of the bone such that it is able to remove bone tissue to form the passage 120. According to another exemplary embodiment, the fixation nail 100 may be formed from a harder material, such as a titanium alloy (Ti-6Al-4V), which has a hardness of approximately 334 HB. At least a portion of the drill bit 202 for use with such a fixation nail may be formed of a material with a hardness that is less than approximately 334 HB, such that it does not damage the fixation nail, but greater than the hardness of the bone such that it is able remove bone tissue to form the passage 120.

According to an exemplary embodiment, the drill bit 202 is formed from a polymer with a hardness that is greater than bone but less than the hardness of the fixation nail 100. For example, the drill bit 202 or a portion of the drill bit 202 may be formed from polyetheretherketone (PEEK), polysulfone (PSU), polyphenylsulfone (PPSU), polyether imide (PEI), or any other suitable polymer or polymer composite material. According to another exemplary embodiment, the drill bit may be formed from a metal or metal alloy with a hardness that is greater than bone but less than the hardness of the fixation nail 100.

Figure 5:
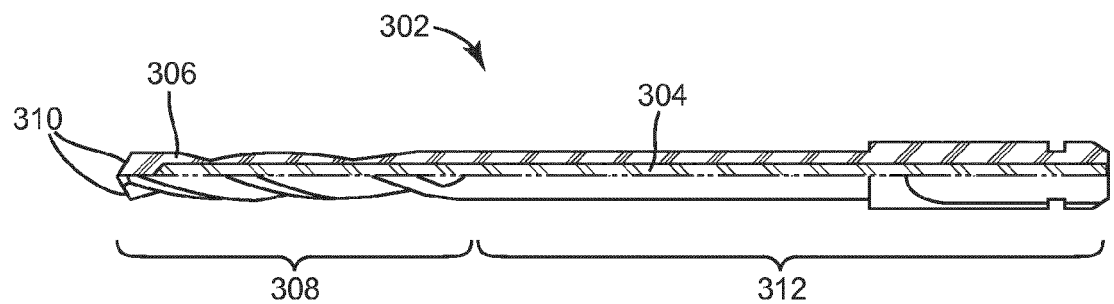
FIG. 5 shows a partial cross-section view of a drill bit for forming a passage for a fixation screw of the fixation system of FIG. 1, according to another exemplary embodiment.

Referring now to FIG. 5, according to another exemplary embodiment, a drill bit 302 may be formed from multiple materials. The drill bit 302 includes an inner portion or core 304 formed from a first material and an outer portion or outer layer 306 formed from a second material that is positioned over the core 304. For example, the core 304 may be formed of a stainless steel alloy (e.g., 316LVM stainless steel), while the outer layer 306 may be polyetheretherketone. The core 304 may be formed of a material that is equal in hardness or harder than the fixation nail. The outer layer 306 may extend over a portion of a drill body 308 (e.g., the forward portion of the drill body 308 proximate a cutting edge 310), over the entire drill body 308, or over the drill body 308 and all or a portion of a shank 312. In this way, the material forming the core 304 may be chosen to achieve a desired structural performance (e.g., stiffness, torsional strength, etc.) of the drill bit 302, while the material forming the outer layer 306 may be chosen to avoid damaging the fixation nail while still being capable of cutting through the bone.

Figure 6:
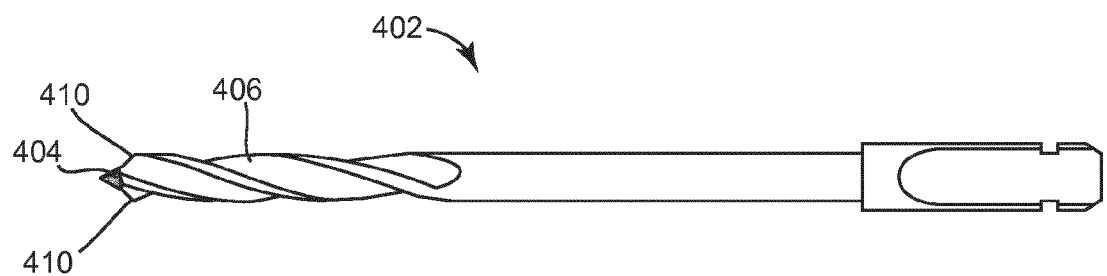
FIG. 6 shows a side view of a drill bit for forming a passage for a fixation screw of the fixation system of FIG. 1, according to another exemplary embodiment.

Referring now to FIG. 6, according to another exemplary embodiment, a drill bit 402 may be formed from multiple materials. The drill bit 402 includes a tip 404 formed from a first material and a main body 406 formed from a second material, with the tip 404 forward of the main body 406. For example, the tip 404 may be formed of a relatively hard material such as a stainless steel alloy (e.g., 416LVM stainless steel) or a titanium alloy, while the main body 406 may be a softer material, such as polyetheretherketone. The tip 404 may be formed of a material that is harder than the fixation nail. The tip 404 may include a portion of a cutting edge 410 (e.g., the interior portion of the cutting edge 410) or may include the entire cutting edge 410. In this way, the material forming the tip 404 may be chosen to achieve a desired penetration of the bone, while the material forming the portions of the drill bit 402 that are most likely to contact the portions of the fixation nail (e.g., the main body 406 and the outer portion of the cutting edges 410) may be chosen to avoid damaging the fixation nail. In some embodiments, a drill bit may include both a core and a tip that is formed from a relatively hard material. The core and the tip may be formed from a continuous body or may be separate bodies which are each coupled to a softer material.

Figure 7:
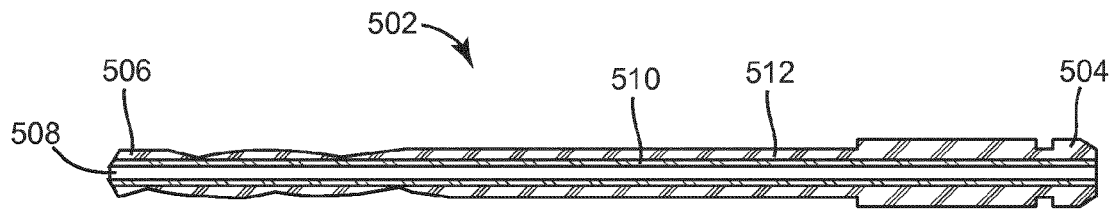
FIG. 7 shows a cross-section view of a drill bit for forming a passage for a fixation screw of the fixation system of FIG. 1, according to another exemplary embodiment.

Referring now to FIG. 7, according to another exemplary embodiment, a drill bit 502 may be cannulated. The drill bit 502 includes a first end 504 and a second end 506 with a drill bit cannulation 508 extending between the ends 504 and 506 and forming openings at each end of the drill bit 502. The drill bit cannulation 508 provides a passage through which an installation device such as a guide wire may pass. After a fixation nail, such as fixation nail 100 has been positioned in a bone, a guide wire may be inserted into the bone and through a bore, such as the bore 118 in the fixation nail 100. The distal end of the guide wire may then be inserted into the drill bit cannulation 508 to align the drill bit 502 with the bore 118 in the fixation nail 100. After forming a passage in the bone, the drill bit 502 may then be removed from the guide wire and the guide wire may be used to facilitate the insertion of a fixation device in the passage. As illustrated in FIG. 7 according to one embodiment, the drill bit cannulation 508 may be formed in a core 510 formed of a first material. An outer layer 512 may be positioned over the core 510 and formed of a second material, similar to the drill bit 302, illustrated in FIG. 5. In other embodiments, the cannulation 508 may be provided in a drill bit formed of a single material, similar to the drill bit 202 illustrated in FIG. 4.

Figure 8:
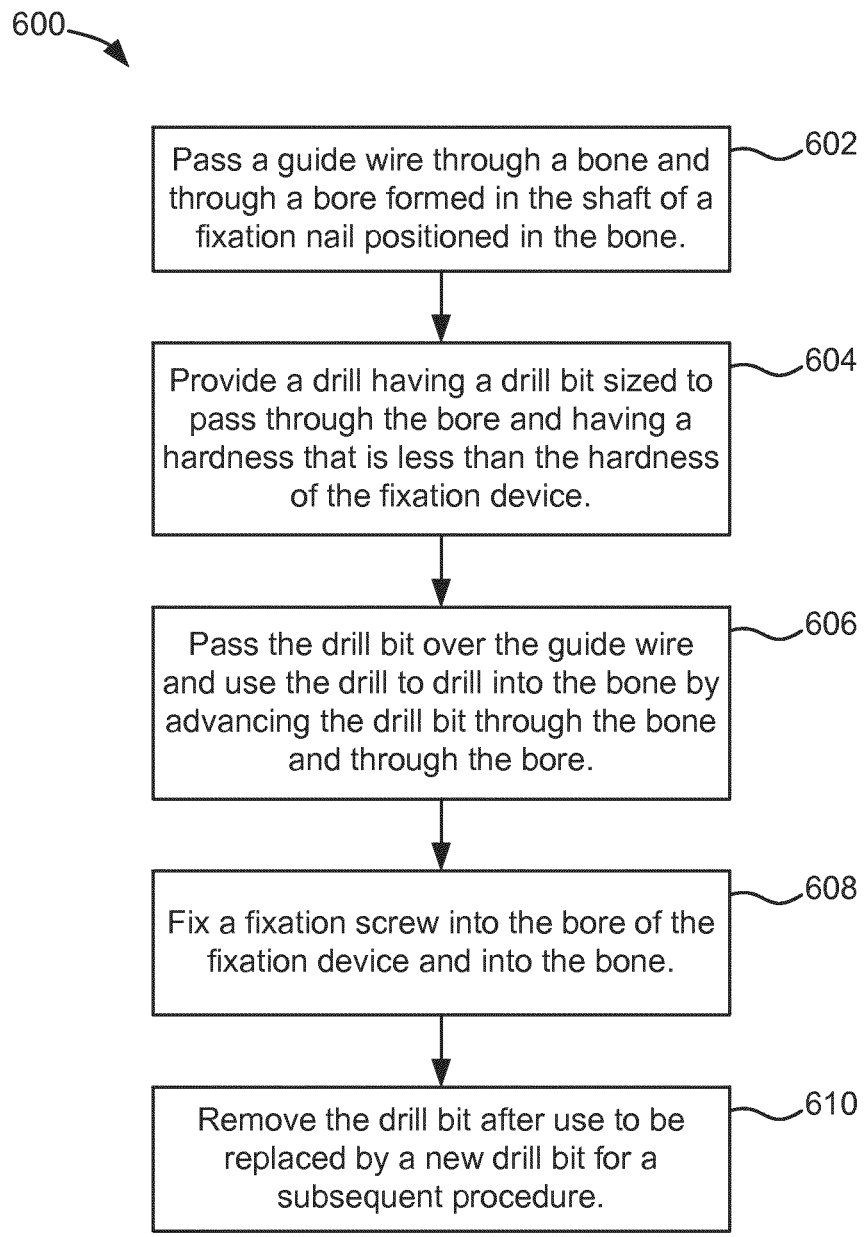
FIG. 8 is a flowchart of a method of preparing a bone to receive a fixation screw through a fixation device, according to an exemplary embodiment.

Referring now to FIG. 8, a method 600 of preparing a bone to receive a fixation screw through a fixation device positioned in a bone is shown according to an exemplary embodiment. The fixation device includes a shaft and at least one bore through the shaft. A guide wire may be optionally placed through the bone and through the bore (step 602). A drill is provided, the drill having a drill bit sized and configured to pass through a bore in the fixation device (step 604). At least an outer portion of the drill bit has a hardness that is less than the hardness of the fixation device. If a guide wire is used, the drill bit is passed over the guide wire. The drill is used to drill into the bone, advancing the drill bit into the bone and through the bore (step 606). Once the drill has formed a passage in the bone aligned with the bore, a fixation screw may be fixed in the bore of the fixation device and into the bone to secure placement of the fixation device in the bone (step 608). The drill bit may be removed from the drill after use to be replaced by a new drill bit for subsequent procedures (step 610).

According to an exemplary embodiment, various components of a fixation system may be packaged together as a kit. For example, a fixation system kit may include a fixation nail formed of a first material and one or more drill bits sized to be received in bores in the fixation nail. The drill bits are least partially formed from a second material specifically selected to have a hardness that is greater than bone but less than the hardness of the fixation nail. By providing the fixation nail and drill bits in a kit, a user does not need to use a preexisting drill bit, which may be as hard or harder than the fixation nail and may potentially damage the fixation nail. The drill bits may be disposable to prevent the future use of a drill bit with a fixation nail that is not as hard as the drill bit. The fixation system kit may further include other devices used to install the fixation nail, such as fixation screws, guide wires, location and aiming jigs and templates, measuring devices, etc.

Other devices may also benefit from being at least partially formed from a material specifically selected to have a hardness that is greater than bone, but less than the hardness of other surgical devices. For example, another rotary tool, such as a reamer used to enlarge and smooth a passage (e.g., the passage 120 formed by the drill bit 202), may have at least an outer portion that is formed of a material such as polyetheretherketone (PEEK) that will not damage the fixation nail 100 formed of a relatively hard material such as stainless steel or a titanium alloy.

While the drill bits 202, 302, 402, and 502 have been described for use with the fixation nail 100, similarly constructed drill bits and other tools may be utilized to advantageously reduce damage to other orthopedic devices in areas (e.g., high stress areas) where they may be inadvertently contacted and damaged by tools or other orthopedic devices. For example, a drill bit for use with a cervical plate may be at least partially formed from a material specifically selected to have a hardness that is greater than the bone being drilled into, but less than the hardness of the plate.

Further modifications and alternative embodiments of various aspects of the invention will be apparent to those skilled in the art in view of this description. Accordingly, this description is to be construed as illustrative only. The construction and arrangements of the bone screws and inserts, as shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, or method steps may be varied or re-sequenced according to alternative embodiments. Other substitutions, modifications, changes and omissions may also be made in the design, operating conditions and arrangement of the various exemplary embodiments without departing from the scope of the present disclosure.

What is claimed is:

1. A bone fixation system, comprising: a fixation device configured to be positioned at a target area of bone comprising two ends connected by a shaft and further comprising a bore formed through the shaft configured to receive a fixation screw; a drill bit sized and configured to pass through the bore to prepare the surrounding bone to receive a second fixation device; wherein at least a distal portion of the drill bit is configured to pass through the bore; wherein the fixation device is made of a first material and wherein the distal portion of the drill bit comprises at least an outer portion made of a second material; and wherein the second material of the drill bit has a hardness that is less than the hardness of the first material of the fixation device, wherein the drill bit comprises an outer sheath formed of the second material positioned over an inner core made of a harder material.

2. The system of claim 1, wherein the second material has a hardness that is greater than the hardness of the portion of the bone being drilled.

3. The system of claim 1, wherein the drill bit is cannulated for receiving a guide wire.

4. The system of claim 1, wherein the second material is polyetheretherketone.

5. The system of claim 1, where in the drill bit is disposable after drilling.

6. The system of claim 1, wherein the shaft of the fixation device is cannulated along at least a portion of its length, and wherein the fixation device comprises at least one fenestration along the cannulated portion of the fixation device shaft.

7. The system of claim 6, wherein the fixation device is adapted to receive an insert portion in the fixation device cannulation.

8. The system of claim 1, wherein the hardness of the second material is greater than the hardness of the bone and less than a Brinell hardness of 160 HB.

9. The system of claim 1, further comprising a fixation screw configured to be received in the bore.

\* \* \* \* \*